(12) United States Patent
Yun et al.

(10) Patent No.: US 8,242,288 B2
(45) Date of Patent: Aug. 14, 2012

(54) METHOD OF PREPARING (6R)-3-HEXYL-4-HYDROXY-6-UNDECYL-5, 6-DIHYDROPYRAN-2-ONE, AND INTERMEDIATE USED IN THE METHOD

(75) Inventors: Sang Min Yun, Seongnam-si (KR); Young Ho Moon, Suwon-si (KR); Young-Kil Chang, Seoul (KR); Dong Jin Hong, Incheon (KR); Ji-Yeon Chang, Seoul (KR); Moon Sub Lee, Bucheon-si (KR); Jaeho Yoo, Seoul (KR); Ji Sook Kim, Yeoju-gun (KR); Cheol Kyung Kim, Suwon-si (KR)

(73) Assignee: Hanmi Holdings Co., Ltd., Seoul (KR)

( * ) Notice: Subject to any disclaimer, the term of this patent is extended or adjusted under 35 U.S.C. 154(b) by 111 days.

(21) Appl. No.: 12/740,827

(22) PCT Filed: Oct. 29, 2008

(86) PCT No.: PCT/KR2008/006371
§ 371 (c)(1),
(2), (4) Date: Apr. 30, 2010

(87) PCT Pub. No.: WO2009/057938
PCT Pub. Date: May 7, 2009

(65) Prior Publication Data
US 2010/0274029 A1 Oct. 28, 2010

(30) Foreign Application Priority Data
Nov. 1, 2007 (KR) .................. 10-2007-0111075

(51) Int. Cl.
*C07D 309/30* (2006.01)

(52) U.S. Cl. ....................................................... 549/292
(58) Field of Classification Search ................... 549/292
See application file for complete search history.

(56) References Cited

U.S. PATENT DOCUMENTS

| | | | |
|---|---|---|---|
| 4,983,746 A | 1/1991 | Barbier et al. | |
| 5,245,056 A | 9/1993 | Karpf et al. | |
| 5,274,143 A | 12/1993 | Ramig et al. | |
| 5,399,720 A | 3/1995 | Karpf et al. | |
| 5,420,305 A | 5/1995 | Ramig et al. | |
| 6,545,165 B1 | 4/2003 | Fleming et al. | |
| 6,552,204 B1 * | 4/2003 | Harrington et al. | 549/292 |
| 2006/0079710 A1 | 4/2006 | Shin et al. | |

OTHER PUBLICATIONS

Marko et al. Journal of the American Chemical Society, 2007, 129, 3516-3517.*
Taiwanese Patent Office, Taiwanese Office Action issued in corresponding TW Application No. 10020558210, dated Jun. 30, 2011.
John J. Landi et al., A new Route to β-Keto- δ -lactones: Practical Preparation of R-3-Hexyl-5,6-dihydro-4-hydroxy-6-undecyl-2H-pyran-2-one,[1a] Key Intermediate in the Asymmetric Synthesis of Tetrahydrolipstatin, Tetrahedron Letters, 1993, pp. 277-280, vol. 34, No. 2, Great Britain.
Written Opinion of ISA in PCT/KR2008/006371, mailed May 4, 2009.

* cited by examiner

*Primary Examiner* — Nizal Chandrakumar
(74) *Attorney, Agent, or Firm* — Sughrue Mion, PLLC

(57) ABSTRACT

Provided is a method of preparing a (6R)-3-hexyl-4-hydroxy-6-undecyl-5,6-dihydropyran-2-one, and a (5R)-2-hexyl-5-hydroxy-3-iminohexadecanoate derivative used in said method as an intermediate.

10 Claims, No Drawings

METHOD OF PREPARING (6R)-3-HEXYL-4-HYDROXY-6-UNDECYL-5,6-DIHYDROPYRAN-2-ONE, AND INTERMEDIATE USED IN THE METHOD

CROSS REFERENCE TO RELATED APPLICATIONS

This application is a National Stage of International Application No. PCT/KR2008/006371 filed Oct. 29, 2008, claiming priority based on Korean Patent Application No. 10-2007-0111075, filed Nov. 1, 2007, the contents of all of which are incorporated herein by reference in their entirety.

FIELD OF THE INVENTION

The present invention relates to a method of preparing a (6R)-3-hexyl-4-hydroxy-6-undecyl-5,6-dihydropyran-2-one, and a (5R)-2-hexyl-5-hydroxy-3-iminohexadecanoate derivative used in said method as an intermediate.

DESCRIPTION OF THE PRIOR ART

An (6R)-3-hexyl-4-hydroxy-6-undecyl-5,6-dihydropyran-2-one of formula (I) which may be in the form of its tautomer, the structure of formula (Ia), is an important intermediate used in the preparation of fine chemicals and pharmaceutical agents (API):

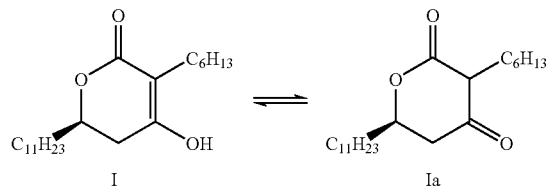

For example, (6R)-3-hexyl-4-hydroxy-6-undecyl-5,6-dihydropyran-2-one is an intermediate used in the synthesis of oxetanones such as tetrahydrolipstatin (Orlistat™), and its preparative methods are disclosed in U.S. Pat. Nos. 4,983,746, 5,245,056, 5,399,720, 5,274,143 and 5,420,305.

U.S. Pat. No. 4,983,746 discloses the preparation of 3,6-dialkyl-5,6-dihydro-4-hydroxy-pyran-2-one by oxidization of dialkyl-3,4,5,6-tetrahydro-4-hydroxy-pyran-2-one using Jone's reagent. However, a strong base such as n-butyl lithium and LDA (lithium diisopropylamide), which are not suitable for industrial applications, is used in the production of dialkyl-3,4,5,6-tetrahydro-4-hydroxy-pyran-2-one, and further reduction of 3,6-dialkyl-5,6-dihydro-4-hydroxy-pyran-2-one is required to obtain the desired optical isomer.

U.S. Pat. Nos. 5,245,056 and 5,399,720 disclose a method comprising the step of preparing (6R)-3-hexyl-4-hydroxy-6-undecyl-5,6-dihydropyran-2-one by activating 3-hydroxytetradecanoic acid with carbonyldiimide, but the yield of this reaction is low, only 34%.

To improve the yield of (6R)-3-hexyl-4-hydroxy-6-undecyl-5,6-dihydropyran-2-one, U.S. Pat. Nos. 5,274,143 and 5,420,305 disclose a method involving intramolecular cyclization of (R)-3-[2-bromo-1-oxooctyloxy]-tetradecanoate in the presence of zinc to produce (6R)-3-hexyl-4-hydroxy-6-undecyl-5,6-dihydropyran-2-one in a yield of 61 to 67%, while U.S. Pat. No. 6,545,165 describes intramolecular cyclization of (R)-3-[2-bromo-1-oxooctyloxy]-tetradecanoate in the presence of tert-butyl magnesium chloride to produce (6R)-3-hexyl-4-hydroxy-6-undecyl-5,6-dihydropyran-2-one in a yield of 78%.

Additionally, U.S. Pat. No. 6,552,204 discloses a process for preparing 3,6-dialkyl-5,6-dihydro-4-hydroxy-pyran-2-one, which comprises: (i) subjecting a protected β-hydroxyacyl halide to a reaction with ketene acetal to obtain an ester of δ-hydroxy-β-enol ether or protected δ-hydroxy-β-enol ether, or (ii) subjecting β-hydroxy acyl halide to a reaction with a malonate half acid to obtain a δ-hydroxy-β-keto ester and then treating the δ-hydroxy-β-keto ester with an acid. However, the starting material must be prepared under a high pressure condition for the production of the desired optical isomer, which leads to process inefficiency.

SUMMARY OF THE INVENTION

It is an object of the present invention to provide an improved method of preparing a (6R)-3-hexyl-4-hydroxy-6-undecyl-5,6-dihydropyran-2-one of formula (I) in a high purity and yield.

It is another object of the present invention to provide an intermediate used in the preparation of the (6R)-3-hexyl-4-hydroxy-6-undecyl-5,6-dihydropyran-2-one of formula (I).

In accordance with an aspect of the present invention, there is provided a method of preparing a (6R)-3-hexyl-4-hydroxy-6-undecyl-5,6-dihydropyran-2-one of formula (I), which comprises:

1) subjecting an (R)-3-hydroxytetradecanenitrile derivative of formula (II) to a reaction with an alkyl 2-bromooctanoate of formula (III) in the presence of zinc to obtain a (5R)-2-hexyl-5-hydroxy-3-iminohexadecanoate derivative of formula (IV);
2) treating the compound of formula (IV) with an aqueous acid to obtain a (5R)-2-hexyl-5-hydroxy-3-oxohexadecanoate derivative of formula (V); and
3) cyclizing the compound of formula (V) under an acidic or basic condition:

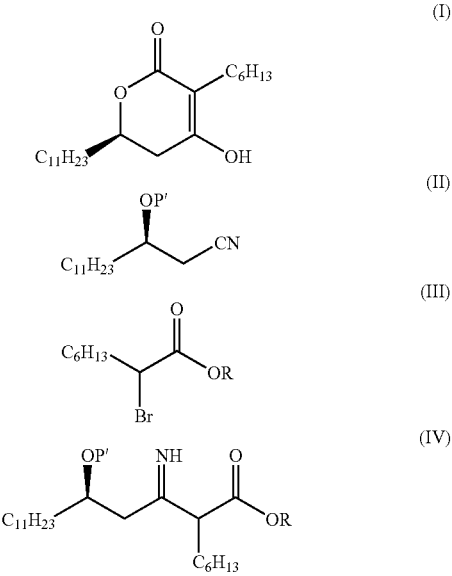

-continued

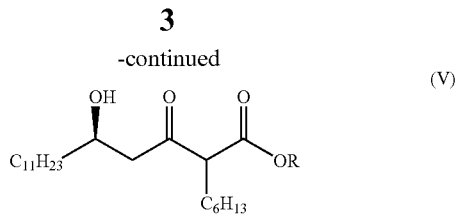
(V)

wherein,

P' is hydrogen or a protecting group selected from trialkylsilyl and alkoxyalkyl which can be removed (deprotected) under an acidic condition, and R is methyl, ethyl, or propyl.

In accordance with the present invention, a compound of formula (I) can be prepared by subjecting (R)-3-hydroxytetradecanenitrile or (R)-3-hydroxytetradecanenitrile having a protected hydroxyl group and a compound of formula (III) to a Blaise reaction in the presence of zinc to obtain a compound of formula (IVa) or a compound of formula (IVb); treating the compound of formula (IVa) or (IVb) with an aqueous acid to obtain a compound of formula (V); and cyclizing the compound of formula (V).

Specifically, the inventive method of preparing the compound of formula (I) may be carried out as shown in Reaction Scheme 1.

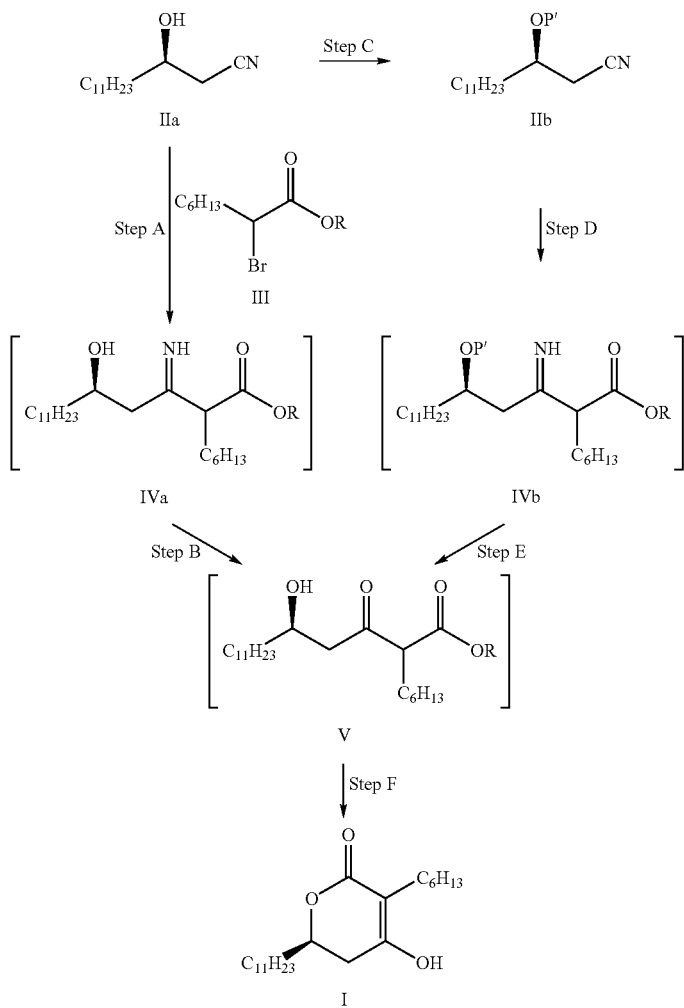

In accordance with another aspect of the present invention, there is provided a compound of formula (IV) used in the preparation of the compound of formula (I).

DETAILED DESCRIPTION OF THE INVENTION

An (R)-3-hydroxytetradecanenitrile derivative of formula (II) used as a starting material in the inventive method may be prepared by the method disclosed in *Tetrahedron Asymmetry* 1999, 2945.

wherein,

P' is a hydroxyl-protecting group selected from trialkylsilyl and alkoxyalkyl which can be deprotected under an acidic condition, and R is methyl, ethyl or propyl.

In step A of Reaction Scheme 1, (R)-3-hydroxytetradecanenitrile of formula (IIa) is subjected to a reaction with an alkyl 2-bromooctanoate of formula (III) in the presence of zinc in a suitable solvent to obtain a (5R)-2-hexyl-5-hydroxy-3-iminohexadecanoate derivative of formula (IVa). Examples of the alkyl 2-bromooctanoate of formula (III) include methyl 2-bromooctanoate, ethyl 2-bromooctanoate and propyl 2-bromooctanoate. The alkyl 2-bromooctanoate is used in an amount ranging from 1 to 10 molar equivalents, preferably 1.5 to 3 molar equivalents, based on 1 mole of (R)-3-hydroxytetradecanenitrile of formula (IIa).

Zinc may be of a powder or dust form which promotes the reaction step A, and an activated zinc powder form is most preferable. The zinc is used in an amount ranging from 1 to 10 molar equivalents, preferably 3 to 5 molar equivalents, based on 1 mole of (R)-3-hydroxytetradecanenitrile of formula (IIa). A catalytic additive for the activation of the zinc may be further used in an amount of 0.01 to 0.2 molar equivalents based on 1 mole of (R)-3-hydroxytetradecanenitrile of formula (IIa). Examples of such an additive include $I_2$, 1,2-dibromoethane, methanesulfonic acid and trimethylsilyl chloride. The trimethylsilyl chloride additive may also be used as a reaction solvent.

Also, for enhancing the reproducibility of step A, a small amount of lead can be used together with zinc. For example, a lead powder may be used in an amount ranging from 2 to 10 wt %, preferably 3 to 5 wt %, based on the total weight of zinc. An example of the use of lead in a zinc-related reaction is disclosed in *Organic Process Research & Development* 2001, 28.

The solvent which may used in step A includes aprotic solvents such as ethyl ether, tetrahydrofuran, 1,4-dioxane, 1,2-dimethoxyethane, acetonitrile, methyl acetate, ethyl acetate, benzene, toluene and a mixture thereof. Among these, ethyl ether, tetrahydrofuran, 1,4-dioxane, 1,2-dimethoxyethane and toluene are preferred.

Step A may be carried out at a temperature ranging from 0° C. to the boiling point of the solvent used, preferably 30 to 100° C.

In step B, the (5R)-2-hexyl-5-hydroxy-3-iminohexadecanoate derivative of formula (IVa) is treated with an aqueous acid in a suitable solvent to obtain a (5R)-2-hexyl-5-hydroxy-3-oxohexadecanoate derivative of formula (V). Examples of the acid include an inorganic acid such as hydrochloric acid, sulfuric acid and hydrobromic acid as well as an organic acid such as toluenesulfonic acid, methanesulfonic acid and camphorsulfonic acid, and the acid is in the form of an aqueous solution in an amount ranging from 0.01 to 5 molar equivalents, preferably 1 to 3 molar equivalents, based on 1 mole of the (5R)-2-hexyl-5-hydroxy-3-iminohexadecanoate derivative of formula (IVa).

The solvent which may used in step B includes protic solvents such as water, methanol, and ethanol; aprotic solvents such as ethyl ether, tetrahydrofuran, 1,4-dioxane, 1,2-dimethoxyethane, acetonitrile, methyl acetate, ethyl acetate, benzene, and toluene; and a mixture thereof.

The (5R)-2-hexyl-5-hydroxy-3-oxohexadecanoate derivative of formula (V) thus obtained may be directly used in step F without further purification.

During step B, a small amount of the (5R)-2-hexyl-5-hydroxy-3-oxohexadecanoate derivative of formula (V) can undergo cyclization to give the target compound, (6R)-3-hexyl-4-hydroxy-6-undecyl-5,6-dihydropyran-2-one of formula (I).

Step B may be carried out at a temperature ranging from 0° C. to the boiling point of the solvent used, preferably 10 to 60° C.

In step C, the hydroxyl group of the (R)-3-hydroxytetradecanenitrile of formula (IIa) is protected by a hydroxyl-protecting group which can be easily deprotected. Exemplary protecting groups include trialkylsilyl such as trimethylsilyl (TMS) and triethylsilyl, and alkoxyalkyl such as tetrahydropyranyl (THP), 4-methoxytetrahydropyranyl (MTHP), 2-methoxy-2-propyl (MOP) and 1-ethoxy-1-ethyl (EE), which may be readily deprotected under an acidic condition.

The trimethylsilylation of the hydroxyl group of (R)-3-hydroxytetradecanenitrile can be carried out by a conventional method (see *Protective groups in organic synthesis* 4th Ed., pp 171-178), and the introduction of a tetrahydropyran protection group can be carried out by a conventional method using dihydrofuran and pyridinium p-toluenesulfonate (see *Protective groups in organic synthesis* 4th Ed., pp 59-68, Protecting groups).

The protected (R)-3-hydroxytetradecanenitrile of formula (IIb) may be used in step D without isolation or purification. In step D, the protected (5R)-2-hexyl-5-hydroxy-3-iminohexadecanoate derivative of formula (IVb) is obtained by a method similar to that used in step A.

In step E, the protected (5R)-2-hexyl-5-hydroxy-3-iminohexadecanoate derivative of formula (IVb) is deprotected under an acidic condition in a manner similar to step B, to obtain the (5R)-2-hexyl-5-hydroxy-3-oxohexadecanoate derivative of formula (V). The (5R)-2-hexyl-5-hydroxy-3-oxohexadecanoate derivative of formula (V) thus obtained may be directly used in step F without further purification.

During step E, a small amount of the (5R)-2-hexyl-5-hydroxy-3-oxohexadecanoate derivative of formula (V) can undergo cyclization to give the target compound, (6R)-3-hexyl-4-hydroxy-6-undecyl-5,6-dihydropyran-2-one of formula (I).

In step F, the (5R)-2-hexyl-5-hydroxy-3-oxohexadecanoate derivative of formula (V) obtained in step B or E is cyclized to obtain the target compound, (6R)-3-hexyl-4-hydroxy-6-undecyl-5,6-dihydropyran-2-one of formula (I). The cyclization may be carried out in a suitable solvent in the presence of an acid or base, as disclosed in U.S. Pat. No. 6,552,204.

The acid or base may be used in an amount ranging from 0.01 to 10 molar equivalents, preferably 0.1 to 3 molar equivalents, based on 1 mole of the (5R)-2-hexyl-5-hydroxy-3-oxohexadecanoate derivative of formula (V).

The examples of the acid include an inorganic acid such as hydrochloric acid and sulfuric acid; an organic acid such as toluenesulfonic acid, methanesulfonic acid and camphorsulfonic acid; and a mixture thereof, while methanesulfonic acid is preferred. Examples of the base include sodium hydroxide and potassium hydroxide.

The solvent which may used in step F includes protic solvents such as water, methanol and ethanol; aprotic solvents such as ethyl ether, tetrahydrofuran, 1,4-dioxane, 1,2-dimethoxyethane, acetonitrile, methyl acetate, ethyl acetate, benzene and toluene; and a mixture thereof, among which acetonitrile is preferred.

The present invention will be described in further detail with reference to Examples. However, it should be understood that the present invention is not restricted by the specific Examples.

Preparation of (6R)-3-hexyl-4-hydroxy-6-undecyl-5,6-dihydropyran-2-one

Example 1

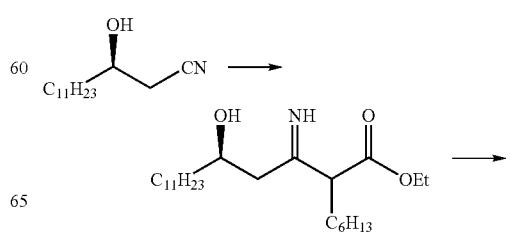

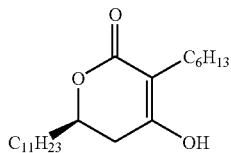

4.35 g of an activated zinc powder, 5 g of (R)-3-hydroxy-tetradecanenitrile and 30 ml of tetrahydrofuran were placed in a reactor and stirred, 0.14 ml of methanesulfonic acid was added thereto, and the resulting mixture was refluxed for 1 hour, to which a dilute solution of 9.53 ml of ethyl 2-bromooctanoate in 10 ml of toluene was added dropwise over about 1 hour and refluxed for 1 hour. The resulting mixture was cooled to room temperature, and 20 ml of 3N HCl was added dropwise thereto over 30 minutes and stirred for about 1 hour. The mixture was heated to about 50° C. and stirred for about 2 hours.

The resulting solid was filtered using a Buchner funnel with a celite pad and washed with 25 ml of ethyl acetate. The organic layer was combined, washed with 50 ml of water, dried over anhydrous magnesium sulfate, and concentrated under a reduced pressure. The concentrate thus obtained was dissolved in 20 ml of acetonitrile, 4.22 g of methanesulfonic acid was added thereto, stirred for about 12 hours, cooled to 5° C. and further stirred for about 2 hours. The solids formed were isolated by filtering, washed with 5 ml of cold acetonitrile and dried, to give 4.85 g of the title compound (yield: 62%) as an off-white solid.

m.p: 110-112° C.

$^1$H-NMR (CDCl$_3$, a mixture of keto and endo forms, ppm): δ 0.80-0.99 (m, 6H), 1.16-2.03 (m, 30H), 2.16-2.80 (m, 2H), 3.22 (t, 0.1H, J=5.5 Hz), 3.41 (t, 0.9H, J=5.5 Hz), 4.25-4.40 (m, 0.1H), 4.48-4.62 (m, 0.1H), 4.62-4.75 (m, 0.8H), 6.75-6.96 (brs, 0.1H)

Example 2

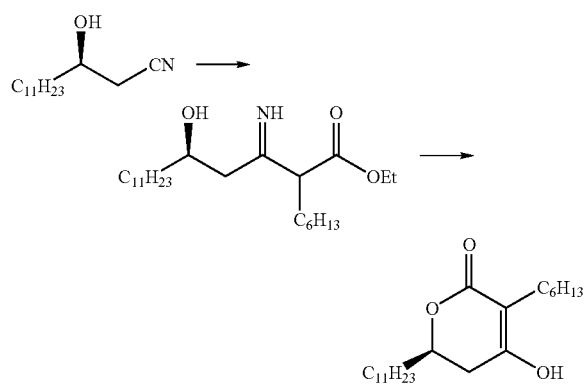

2.9 g of an activated zinc powder and 10 ml of tetrahydrofuran were placed in a reactor and stirred, 6 ml of chlorotrimethyl silane was added thereto, and the resulting mixture was refluxed for 1 hour, to which a dilute solution of 2 g of (R)-3-hydroxy tetradecanenitrile in 4 ml of tetrahydrofuran was slowly added over about 5 minutes and stirred for about 5 minutes. Subsequently, a dilute solution of 5.6 ml of ethyl 2-bromooctanoate in 4 ml of tetrahydrofuran was added dropwise over 30 minutes and refluxed for 1 hour. The resulting mixture was cooled to about 5° C., 6 ml of 3N HCl was added dropwise thereto over 30 minutes. The mixture was heated to about 50° C. and stirred for 1 hour.

The resulting solid was filtered using a Buchner funnel with a celite pad and washed with 20 ml of ethyl acetate. The organic layer was combined, washed with 20 ml of water and 20 ml of brine, dried over anhydrous magnesium sulfate, and concentrated under a reduced pressure. The oily residue thus obtained was dissolved in 10 ml of acetonitrile, 1.5 g of methansulfonic acid was added thereto, stirred for 12 hours at room temperature. The solids formed were isolated by filtering, washed with 2 ml of cold acetonitrile and dried, to give 1.0 g of the title compound (yield: 32%) as an off-white solid.

$^1$H-NMR (CDCl$_3$, a mixture of keto and endo forms, ppm): δ 0.80-0.99 (m, 6H), 1.16-2.03 (m, 30H), 2.16-2.80 (m, 2H), 3.22 (t, 0.1H, J=5.5 Hz), 3.41 (t, 0.9H, J=5.5 Hz), 4.25-4.40 (m, 0.1H), 4.48-4.62 (m, 0.1H), 4.62-4.75 (m, 0.8H), 6.75-6.96 (brs, 0.1H)

Example 3

Step 1: Preparation of (R)-3-[tetrahydropyran-2-yl-oxy]-tetradecanenitrile

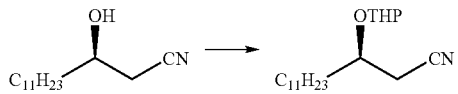

2.16 g of (R)-3-hydroxy-tetradecanenitrile, 1.93 ml of dihydropyran and 20 ml of tetrahydrofuran were placed in a reactor and stirred, and 266 mg of pyridinium p-toluenesulfonate was added thereto, heated to 50° C., and stirred for about 2 hours. The mixture was cooled to room temperature, 30 ml of water and 30 ml of hexane were added thereto, and stirred vigorously for 5 minutes. The resulting mixture was allowed to undergo phase separation and the aqueous layer was removed. The organic layer was dried over anhydrous magnesium sulfate and concentrated under a reduced pressure, to give 2.97 g of the title compound (yield: 100%) as an oil.

$^1$H-NMR (CDCl$_3$, a mixture of keto and endo forms, ppm): δ 0.80-0.99 (m, 6H), 1.16-2.03 (m, 30H), 2.16-2.80 (m, 2H), 3.22 (t, 0.1H, J=5.5 Hz), 3.41 (t, 0.9H, J=5.5 Hz), 4.25-4.40 (m, 0.1H), 4.48-4.62 (m, 0.1H), 4.62-4.75 (m, 0.8H), 6.75-6.96 (brs, 0.1H)

Step 2: Preparation of 5,6-dihydro-3-hexyl-4-hydroxy-6-undecyl-2H-pyran-2-one

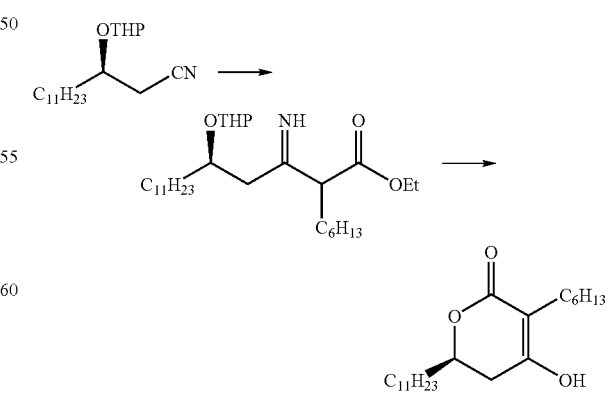

1.27 g of an activated zinc powder, 2.0 g of (R)-3-[tetrahydropyran-2-yl-oxy]-tetradecanenitrile obtained in Step 1, and 8 ml of tetrahydrofuran were placed in a reactor and stirred, and 0.07 ml of methanesulfonic acid was added thereto. The mixture was then refluxed for 1 hour, a solution of 2.77 ml of ethyl 2-bromooctanoate dissolved in 4 ml of tetrahydrofuran was added dropwise thereto over about 1 hour and further refluxed for 1 hour.

The resulting mixture was cooled to about 5° C., 8 ml of 3N HCl was added dropwise thereto over 30 minutes, and stirred for about 2 hours at 40° C. The resulting solid was filtered using a Buchner funnel with a celite pad and washed with 5 ml of ethyl acetate. The organic layer was combined, washed with 50 ml of water, dried over anhydrous magnesium sulfate, and concentrated under a reduced pressure. The oily residue thus attained was dissolved in 8 ml of acetonitrile, 0.12 g of methansulfonic acid was added thereto, stirred for 5 hours at room temperature, cooled to 5° C. and further stirred for about 1 hour. The solids formed were isolated by filtering, to give 1.46 g of the title compound (yield: 64%) as an off-white solid.

$^1$H-NMR (CDCl$_3$, a mixture of keto and endo forms, ppm): δ 0.80-0.99 (m, 6H), 1.16-2.03 (m, 30H), 2.16-2.80 (m, 2H), 3.22 (t, 0.1H, J=5.5 Hz), 3.41 (t, 0.9H, J=5.5 Hz), 4.25-4.40 (m, 0.1H), 4.48-4.62 (m, 0.1H), 4.62-4.75 (m, 0.8H, 6.75-6.96 (brs, 0.1H)

Example 4

Step 1: Preparation of (R)-3-[trimethylsilyloxy]-tetradecanenitrile

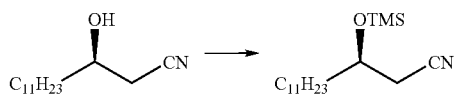

5 g of (R)-3-hydroxy-tetradecanenitrile and 35 ml of methylene chloride were placed in a reactor and stirred. The mixture was cooled to 0° C., and 3.87 ml of triethylamine was added thereto, to which 3.38 ml of trimethylsilyl chloride was added over about 30 minutes, and stirred for about 1 hour. Subsequently, the resulting mixture was slowly heated to room temperature and stirred for about 1 hour, 50 ml of water was added thereto, and stirred vigorously for 5 minutes. The aqueous layer was removed. The organic layer was combined with 50 ml of water, dried over anhydrous magnesium sulfate and concentrated under a reduced pressure, to give 6.66 g of the title compound (yield: 100%) as an oil.

$^1$H-NMR (CDCl$_3$, ppm): δ 0.15 (s, 9H), 0.88 (t, 3H, J=6.7 Hz), 1.18-1.43 (m, 18H), 1.18-1.65 (m, 2H), 2.44 (dd, 2H, J=5.7 Hz), 3.82-4.00 (m, 1H)

Step 2: Preparation of 5,6-dihydro-3-hexyl-4-hydroxy-6-undecyl-2H-pyran-2-one

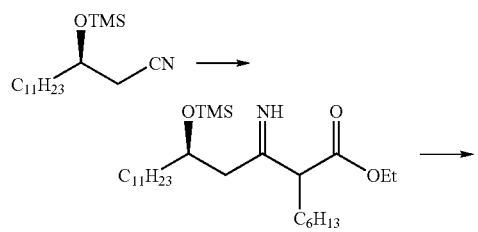

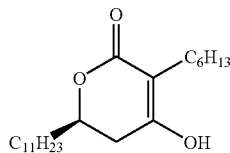

2.2 g of an activated zinc powder, 10 ml of tetrahydrofuran and 0.02 ml of methanesulfonic acid were placed in a reactor, and the resulting mixture was refluxed for 1 hour, to which a dilute solution of 2 g of (R)-3-trimethylsilyloxy tetradecanenitrile obtained in step 1 in 4 ml of tetrahydrofuran was slowly added over about 5 minutes and further stirred for about 5 minutes. A dilute solution of 3.6 ml of ethyl 2-bromooctanoate in 4 ml of tetrahydrofuran was added dropwise thereto over 30 minutes and further refluxed for 1 hour.

The resulting mixture was cooled to about 5° C., 6 ml of 3N HCl was added dropwise thereto over 30 minutes, and stirred for 2 hours at 40° C. The resulting solid was filtered using a Buchner funnel with a celite pad and washed with 20 ml of ethyl acetate. The organic layer was combined, washed with 20 ml of water and 20 ml of brine, dried over anhydrous magnesium sulfate, and concentrated under a reduced pressure. The oily residue thus attained was dissolved in 10 ml of acetonitrile, 1.1 g of methansulfonic acid was added thereto, and stirred for 12 hours at room temperature. The solids formed were isolated by filtering, to give 1.54 g of the title compound (yield: 65%) as an off-white solid.

$^1$H-NMR (CDCl$_3$, a mixture of keto and endo forms, ppm): δ 0.80-0.99 (m, 6H), 1.16-2.03 (m, 30H), 2.16-2.80 (m, 2H), 3.22 (t, 0.1H, J=5.5 Hz), 3.41 (t, 0.9H, J=5.5 Hz), 4.25-4.40 (m, 0.1H), 4.48-4.62 (m, 0.1H), 4.62-4.75 (m, 0.8H, 6.75-6.96 (brs, 0.1H)

While the invention has been described with respect to the specific embodiments, it should be recognized that various modifications and changes may be made by those skilled in the art to the invention which also fall within the scope of the invention as defined as the appended claims.

What is claimed is:

1. A method of preparing a (6R)-3-hexyl-4-hydroxy-6-undecyl-5,6-dihydropyran-2-one of formula (I), which comprises:
    1) subjecting a compound of formula (II) to a reaction with a compound of formula (III) in the presence of zinc;
    2) treating a resulting reaction mixture with an aqueous acid to produce a precipitate;
    3) washing the precipitate with an organic solvent to obtain an organic layer; and
    4) subjecting the organic layer to a cyclization under an acidic condition to obtain (6R)-3-hexyl-4-hydroxy-6-undecyl-5,6-dihydropyran-2-one of formula (I):

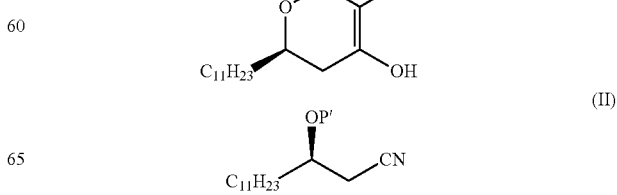

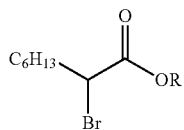 (III)

wherein,
P' is hydrogen or a protecting group selected from trialkylsilyl and alkoxyalkyl which can be deprotected under an acidic condition, and
R is methyl, ethyl, or propyl.

2. The method of claim 1, wherein P' is hydrogen, and R is methyl, ethyl, or isopropyl.

3. The method of claim 1, wherein the alkoxyalkyl moiety is tetrahydropyranyl, 4-methoxytetrahydropyranyl, 2-methoxy-2-propyl, or 1-ethoxy-1-ethyl.

4. The method of claim 1, wherein the compound of formula (III) is methyl 2-bromooctanoate, ethyl 2-bromooctanoate or propyl 2-bromooctanoate.

5. The method of claim 1, wherein zinc is used in an amount ranging from 1 to 10 molar equivalents, based on 1 mole of the compound of formula (II) used in step 1).

6. The method of claim 1, wherein step 1) further comprises adding an additive selected from the group consisting of $I_2$, 1,2-ethanedibromide, methanesulfonic acid, and trimethylsilyl chloride.

7. The method of claim 1, wherein step 1) further comprises adding lead.

8. The method of claim 1, wherein step 1) is carried out in a solvent selected from the group consisting of ethyl ether, tetrahydrofuran, 1,4-dioxane, 1,2-dimethoxyethane, acetonitrile, methyl acetate, ethyl acetate, benzene, toluene, and a mixture thereof.

9. The method of claim 1, wherein the acid used in step 2) is an inorganic acid selected from the group consisting of hydrochloric acid, sulfuric acid, and hydrobromic acid; an organic acid selected from the group consisting of toluenesulfonic acid, methanesulfonic acid, and camphorsulfonic acid; or a mixture thereof.

10. The method of claim 1, wherein step 2) is carried out in a protic solvent selected from the group consisting of water, methanol, and ethanol; an aprotic solvent selected from the group consisting of ethyl ether, tetrahydrofuran, 1,4-dioxane, 1,2-dimethoxyethane, acetonitrile, methyl acetate, ethyl acetate, benzene, and toluene; or a mixture thereof.

* * * * *